United States Patent [19]

Darby et al.

[11] Patent Number: 4,605,772

[45] Date of Patent: Aug. 12, 1986

[54] PROCESS FOR PREPARING N-ALKANE-N-ALKANOLAMINES

[75] Inventors: Nicholas Darby, Toronto; Gordon C. Dunmore, Ft. Saskatchewan, both of Canada

[73] Assignee: The Dow Chemical Company, Midland, Mich.

[21] Appl. No.: 685,529

[22] Filed: Dec. 24, 1984

[51] Int. Cl.[4] .................. C07C 91/04; C07C 91/12; C07C 91/10; C07C 87/06
[52] U.S. Cl. .................................. 564/503; 564/506; 564/463
[58] Field of Search ................ 564/506, 503, 463

[56] References Cited

U.S. PATENT DOCUMENTS 3,636,114 1/1972 Tobler et al. ................ 564/503

OTHER PUBLICATIONS

Spialter and Pappalardo, The Acyclic, Aliphatic Tertiary Amines (1965), pp. 79–80.
Wagner and Zook, Synthetic Organic Chemistry (1953), pp. 43 and 666–668.

*Primary Examiner*—Charles F. Warren
*Assistant Examiner*—R. A. Picard
*Attorney, Agent, or Firm*—Jeffrey S. Boone; Christopher John Rudy

[57] ABSTRACT

N-alkane-N-alkanolamines are prepared by (a) contacting an N-alkane-N-alkanolamine having more N-alkanolamine moieties than the product compound, with a haloalkane; (b) contacting the product of step (a) with a strong base; and (c) deprotonating the product of step (b). The method of the invention produces relatively pure compounds in high yield, from low-value starting materials. The compounds produced by the invention are useful for the absorption of sulfur compounds from gases produced by the combustion of sulfur-containing hydrocarbon materials.

15 Claims, No Drawings

PROCESS FOR PREPARING N-ALKANE-N-ALKANOLAMINES

BACKGROUND OF THE INVENTION

This invention relates to the production of N-alkane-N-alkanolamines from compounds having more N-alkanol moieties than the product compound.

N-alkane-N-alkanolamines, such as N-methyldiethanolamine, $CH_3-N-(CH_2CH_2OH)_2$, are well-known. They have many commercial uses, including uses as an absorbent for the removal of sulfur compounds from gases produced by the combustion of sulfur-containing hydrocarbon materials.

Processes for making N-alkane-N-alkanolamines are well-known. For instance, the following reaction sequence, taught by J. March, *Advanced Organic Chemistry*, 2nd Ed., 1977, pp. 377-378, McGraw-Hill, NY, is well-known:

$$H-N-(CH_2CH_2OH)_2 + CH_3Cl \rightarrow C-H_3-N-(CH_2CH_2OH)_2 \cdot HCl \rightarrow C-H_3-N-(CH_2CH_2OH)_2.$$

Yet another process taught by the above-cited reference is:

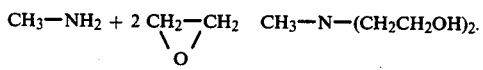

SUMMARY OF THE INVENTION

Briefly, the invention is a method for preparing an N-alkane-N-alkanolamine of the structure

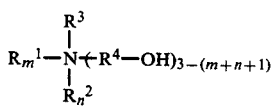

by (a) contacting a compound of the structure

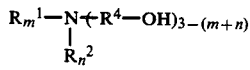

with a haloalkane of the structure $R^3X$; (b) contacting the product of step (a) with a strong base; and (c) deprotonating the product of step (b).

The method of the invention produces relatively pure compounds in high yield, from low-value starting materials.

DETAILED DESCRIPTION OF THE INVENTION

In the specification and claims, numerical ranges are not critical unless otherwise stated. That is, the numerical ranges may be read as if they were prefaced with the word "about" or "substantially".

In the instant invention, compounds are prepared which have the structure:

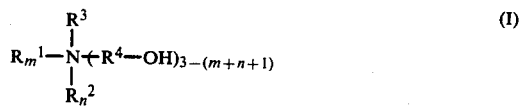

wherein $R^1$, $R^2$, and $R^3$ are each independently hydrocarbon moieties having from 1 to 12, preferably 1 to 6, more preferably 1 to 4, and most preferably 1 to 3 carbon atoms; each $R^4$ is independently a hydrocarbon moiety having 1 to 6, preferably 2 to 4, more preferably 2 or 3, and most preferably 2 carbon atoms; m and n are each independently 0, 1, or 2, provided that m and n are such that the nitrogen atom of formula (I) has a valence of 3. The notation $(R^4-OH)$ is intended to include primary, secondary, and tertiary alcohol moieties. Thus, for example, the $(R^4-OH)$ group may be $$(CH_2-CH-CH_3).$$
$$\quad\quad |$$
$$\quad\quad OH$$

The starting material for use in the invention has the structure:

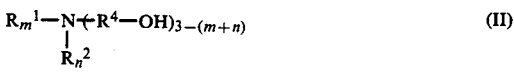

wherein $R^1$, $R^2$, $R^4$, m, and n are as defined for formula (I) above. A preferred starting material is that where each $R^4$ is a $C_2$ moiety and m and n are both zero (triethanolamine). These starting materials are typically produced as by-products from various amine syntheses, and are commercially available.

Although referred to as "N-alkane-N-alkanolamines", the starting compound (II) need not have any $R^1$ and $R^2$ moieties, and the product compound (I) need not have any $(R^4-OH)$ moieties.

The compound of formula (II) is reacted with a haloalkane of the formula:

$$R^3X \quad\quad (III)$$

wherein $R^3$ is as defined for formula (I) above; and X is a halogen, preferably fluorine, chlorine, bromine or iodine, more preferably chlorine, bromine, or iodine, and most preferably chlorine. The product resulting from the reaction of (II) and (III) is presumed to have the structure:

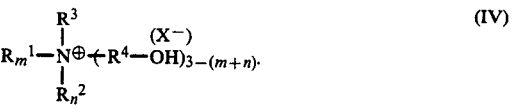

The product, (IV), is then subjected to treatment with a strong base to replace the halogen ion with an oxygen-containing negative ion. The resulting product is then deprotonated to yield a product having the structure of formula (I).

The reaction of the initial starting material (II) with the haloalkane (III) may be accomplished in a wide variety of conditions. If the starting material is not in a liquid state, it is conveniently dissolved in a suitable solvent such as acetone, water, dimethylformamide, or an alkanol. Excess solvent will, however, slow the reaction rate. Reaction pressure, temperature, and time are not critical. The reaction can take place under ambient conditions, but conveniently takes place at an elevated temperature (up to the decomposition temperature of the materials), preferably 30° C. to 200° C., more preferably 80° C. to 120° C.; and elevated pressure (as necessary to keep the reactants liquid or dissolved), preferably 0 to 3000 kPa (absolute), more preferably 100 to 2000 kPa (absolute), most preferably 200 to 2000 kPa (absolute); will cause the reaction to proceed more quickly. The reactants may be reacted for a wide variety of times, preferably 1 minute to 48 hours, more preferably 1 to 4 hours. While either reactant may be present in a great molar excess, there is generally no reason for doing such. A ratio of amine compound (II) to haloalkane (III) of 10:1 to 1:10 is acceptable. A preferred ratio is 1:1 to 1:2, preferably 1:1 to 1:1.3. A ratio of 1:1.1 is considered to be the optimum under most circumstances.

The halogenated product (IV) is conveniently purified before the next reaction step. The reaction mixture can be cooled to cause precipitation of the product which can then be separated by filtration and washed.

The conversion of the halide (IV) takes place with a strong base. As the strong base, virtually any reagent stronger than the negative halide ion may be used. The use of sodium hydroxide or silver oxide will replace the halide ion with a hydroxide ion. The use of sodium methoxide will result in a methoxide. A preferred strong base reagent is a strong base ion-exchange resin such as DOWEX ® MSA-1 resin (available from The Dow Chemical Company, Midland, Mich., USA). The use of an ion-exchange resin permits rapid separation of the product from the by-product and greatly enhances the economic viability of this invention.

The conversion of the halide (IV) with the strong base can take place under a variety of conditions, which can be similar to the conditions for the halogenation step. The reaction desirably takes place in a solvent at 0° C. to 100° C., more desirably 30° C. to 60° C.; at 100 to 700 kPa (absolute). Reaction times can vary from less than 1 minute to several hours. If an ion-exchange resin is used, the resulting product and solvent may be transferred directly to the next reaction step without further purification.

After conversion of the halide (IV) with the strong base, the resulting compound is deprotonated, removing an $\ce{-(R^4-OH)}$ moiety, to yield the final product (I). The deprotonation can take place with any strongly basic counterion capable of initiating deprotonation. Although not preferred, the deprotonation can take place by the application of high temperature. Useful reagents include primary amines and alkoxides. A particularly preferred reagent is ammonia, because it can react with the removed $\ce{-(R^4-OH)}$ moiety (which is in the form of an epoxyalkane) to form an alkanolamine, which is easily separated from the reaction mixture and which is itself a valuable product.

The deprotonation reaction may take place over a variety of conditions. A solvent, such as water or an alkanol, may be used. The temperature is desirably 60° C. to 300° C., preferably 100° C.-140° C. The pressure is desirably 0 to 3000 kPa, preferably 700 to 2000 kPa (absolute). The reaction time may vary from about 2 seconds to 24 hours, preferably 2 seconds to 16 hours.

The final product is conveniently purified by vacuum distillation. If the resulting product (I) has an $\ce{-(R^4-OH)}$ moiety, it can be considered a starting material (II), and the entire reaction sequence repeated.

If the starting material (II) has more than one $\ce{-(R^4-OH)}$ moiety, there may be some preference for the removal of some moieties over others. Although selectivity has not been thoroughly investigated, it is believed that a $\ce{-(CH_2-CH_2OH)}$ moiety would be more likely to be removed than other $\ce{-(R^4-OH)}$ groups.

EXAMPLE 1

Part A: halogenation

Triethanolamine (TEA) (60.0 g, 0.402 mole) was dissolved in acetone (74.2 g) in a 300-ml high pressure reactor. The reactor was sealed and purged with $N_2$. Chloromethane (methyl chloride) (21.1 g, 0.418 mole) was added to the vessel, which was subsequently pressurized to 50 psig (350 kPa, gauge) with nitrogen. The mixture was agitated and the vessel heated to 100° C. After 2 hours at this temperature, no further pressure drop was observed, and the vessel was cooled to 20° C., vented and opened. The mixture was filtered to give a white hygroscopic solid, which was quickly washed with dry acetone and transferred to a vacuum desiccator. The dried product, N-methyltriethanolammonium chloride, weighed 75.8 g (0.380 mole). Unreacted TEA (2.64 g, 0.0177 mole) was recovered from the mother liquor. Additional product (1.12 g) was recovered from washing the filtration equipment with water.

Part B: treatment with strong base

N-methyltriethanolammonium chloride (20.0 g, 0.100 mole) was dissolved in deionized water (113 g). This solution was passed through a chromatography column packed with 350 g of DOWEX ® MSA-1 ion-exchange resin. The basic fraction eluting from the column was collected as product. This solution was concentrated to approximately 100 g. The quantity of N-methyltriethanolammonium hydroxide in this solution was (17.7 g, 0.0977 mole, analysis by titration).

Part C: deprotonation

A solution of N-methyltriethanolammonium hydroxide (16.7 g) in water (82.7 g) was placed in a 600-ml stainless steel, high pressure reactor, along with aqueous ammonia (135 ml of 14.8M sol). The reactor was sealed and pressurized to 100 psig (700 kPa, gauge) with nitrogen, then heated to 120° C. with mechanical agitation for 16 hours. The reactor was allowed to cool and the pressure was released. The contents were reduced in volume and distilled under reduced pressure to furnish 15.0 g of distillate, consisting of N-methyldiethanolamine and ethanolamine, collected over the range of 38° C.-92° C./0.15-0.50 mm Hg (20-70 kPa). A trace amount of a high boiling impurity was present in the last few ml of distillate.

What is claimed is:

1. A method of producing an N-alkane-N-alkanolamine of the structure

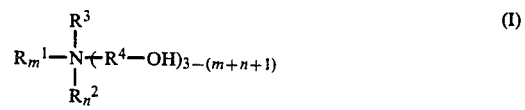

wherein $R^1$, $R^2$, and $R^3$ are each independently hydrocarbon moieties having from 1 to 12 carbon atoms; each $R^4$ is independently a hydrocarbon moiety having 1 to 6 carbon atoms; and m and n are each independently 0, 1, or 2, provided that m and n are such that the nitrogen atom of (I) has a valence of 3; comprising (a) contacting a compound of the structure

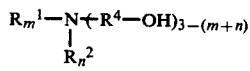

$$R_m^1-N(-R^4-OH)_{3-(m+n)} \quad \text{(II)}$$
$$\underset{R_n^2}{|}$$

wherein $R^1$, $R^2$, $R^4$, m, and n are as defined above, with a haloalkane of the structure $R^3X$, wherein $R^3$ is as defined above; and X is a halogen;

(b) contacting the product of step (a) with a strong base; and (c) deprotonating the product of step (b).

2. The method of claim 1 wherein $R^1$, $R^2$, $R^3$, and $R^4$ each have 1 to 3 carbon atoms.

3. The method of claim 2 wherein $R^1$, $R^2$, and $R^4$ each have 2 carbon atoms, and $R^3$ has 1 carbon atom.

4. The method of claim 1 wherein X is chlorine.

5. The method of claim 1 wherein in step (a), compound (II) is dissolved in a solvent, and the contact takes place at a temperature greater than 80° C. and a pressure greater than 200 kPa (absolute).

6. The method of claim 1 wherein in step (b), the strong base is a strong base ion-exchange resin.

7. The method of claim 6 wherein in step (b), the contact takes place in the presence of a solvent.

8. The method of claim 1 wherein in step (c) the deprotonation takes place by contacting the product of step (b) with a deprotonation reagent.

9. The method of claim 8 wherein the deprotonation reagent is a primary amine or ammonia.

10. The method of claim 8 wherein the deprotonation reagent is ammonia.

11. The method of claim 10 additionally comprising
(d) separating the reaction product of the ammonia and $-R^4-OH$).

12. The method of claim 1 wherein compound (II) has at least two $-R^4-OH$) moieties, and steps (a)-(c) are conducted at least twice.

13. The method of claim 12 wherein in step (c) the deprotonation takes place by contacting the product of step (b) with a deprotonation reagent.

14. The method of claim 13 wherein the deprotonation reagent is a primary amine or ammonia.

15. The method of claim 13 wherein the deprotonation reagent is ammonia.

* * * * *